US006207658B1

(12) United States Patent
Simpkins et al.

(10) Patent No.: US 6,207,658 B1
(45) Date of Patent: *Mar. 27, 2001

(54) PRESERVATION OF TISSUE DURING REMOVAL STORAGE AND IMPLANTATION

(75) Inventors: James W. Simpkins; Pattie S. Green; Kelly E. Gridley, all of Gainesville, FL (US)

(73) Assignee: University of Florida Research Foundation, Inc., Gainesville, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 09/128,862

(22) Filed: Aug. 4, 1998

Related U.S. Application Data

(60) Division of application No. 08/782,883, filed on Jan. 10, 1997, now Pat. No. 5,824,672, which is a continuation-in-part of application No. 08/685,574, filed on Jul. 24, 1996, now Pat. No. 5,859,001.
(60) Provisional application No. 60/009,705, filed on Jan. 11, 1996.

(51) Int. Cl.[7] ............................. A61K 31/56; A61K 31/35
(52) U.S. Cl. ............................................. 514/182; 514/455
(58) Field of Search ..................................... 514/182, 455

(56) References Cited

U.S. PATENT DOCUMENTS

| 5,002,965 | 3/1991 | Ramwell et al. ............... 514/468 |
| 5,051,352 | 9/1991 | Martindale et al. ............... 435/1 |
| 5,811,438 | * 9/1998 | Hellberg et al. ............... 514/458 |
| 5,824,672 | * 10/1998 | Simpkins et al. ............... 514/182 |
| 5,859,001 | 1/1999 | Simpkins et al. ............... 514/182 |

FOREIGN PATENT DOCUMENTS

| WO94/22451 | 10/1994 | (WO) . |
| WO 94/26261 | 11/1994 | (WO) . |
| WO95/13076 | 5/1995 | (WO) . |
| WO 95/18108 | 7/1995 | (WO) . |
| WO 95/19768 | 7/1995 | (WO) . |
| WO 95/34301 | 12/1995 | (WO) . |

OTHER PUBLICATIONS

Demirbas et al., Transplantation Proceedings, (1993), vol. 25, p. 2274.

(List continued on next page.)

Primary Examiner—Frederick Krass
Assistant Examiner—Donna Jagoe
(74) Attorney, Agent, or Firm—Bromberg & Sunstein LLP

(57) ABSTRACT

A method is provided for preserving tissues during removal, storage and implantation into a subject by enhancing cell viability in a population of graft cells during the transplantation procedure. The method includes selecting an effective dose of a polycylic phenolic compound in a physiologically acceptable formulation and exposing at least the population of graft cells to the formulation containing the compound within a time that is effectively proximate to the transplantation procedure so as to confer cytoprotection on the population of graft cells.

19 Claims, 3 Drawing Sheets

OTHER PUBLICATIONS

Foegh M.D., DSc., *Journal of Heart and Lung Transplantation*, (1995), vol. 14, pp. S170–172.

Ikeda et al., (1996), *Life Sciences*, vol. 59, pp. 781–788.

Laue et al., (1995), Transplantation Proceedings, (1995), vol. 27, pp. 1875–1876.

Foegh et al., "Estrogen and Prevention of Transplant Atherosclerosis", The Journal of Heart and Lung Transplantation, 1995.

Miller et al., "Neoromodulatin of Transplanted Gonadotropin–Releasing Hormone Neurons in Male and Female Hypogonadal Mice with Preoptic Area Brain Grafts", Biology of Reproduction, 1995.

Behl, Christian, et al, *Biochemical and Biophysical Research Communications*, (1992); vol. 186, No. 2, pp. 944–950.

Behl, Christian, et al, *Biochemical and Biophysical Research Communications*, (1995); vol. 216, No. 2, pp. 473–482.

Boyd, Gwendolyn L, et al, *Arch. Surg.*, (1996), vol. 131, pp. 160–165.

Braughler, J. Mark, et al, *The Journal of Biological Chemistry*, (1987), vol. 262, No. 22, pp. 10438–10440.

Clark, James H., et al, *Journal of Steroid Biochemistry*, (1982), vol. 16, pp. 323–328.

Clark, James H., et al, *Pharmacy Ther.*, (1983), vol. 21, pp. 429–453.

Dimlich, R.V.W., et al, *Advances in Neurology*, (1990), vol. 52, pp. 365–375.

Goodwin, C.J., et al, *Journal of Immunological Methods*, (1995), vol. 179, pp. 95–103.

Hirasawa, K., et al, Transplanation Proceedings, (1992), vol. 24, No. 1, pp. 408–409.

Huggins, Charles, et al, *Journal of Experimental Medicine*, (1954), vol. 100, pp. 225–243.

Hung, C.J., et al, Transplantation Proceedings, (1996), vol. 28, No. 3(Jun.), pp. 1548–1550.

Jacobsen, E. Jon, et al, *Journal Medical Chemistry*, (1990), vol. 33, pp. 1145–1151.

Korenman, Stanley G., *Steroids*, (1969), vol. 13, pp. 163–177.

Levitt, M. Andrew, *Journal of Cardiovascular Pharmacology*, (1994), vol. 23, pp. 136–140.

Mooradian, Arshag, *J. Steroid Biochem. Molec. Biol.*, (1993), vol. 45, No. 6, pp. 503–511.

Nakano, Minoru, et al, *Biochemical and Biophysical Research Communication*, (1987), vol. 142, No. 3, pp. 919–924.

Papendorp, John T., *Journal of Cellular Physiology*, (1985), vol. 125, pp. 591–595.

The STIPAS Investigators, *Stroke*, (1994), vol. 25, No. 2, pp. 418–423.

Sugioka, Katsauki, et al, *Federation of European Biochemical Societies*, (1987), vol. 210, No. 1, pp. 37–39.

Tanaka, Kazunori, et al, *Nippon–Naibunpi–Gakkai–Zasshi*, (1993), vol. 69, pp. 534–540.

Uhler, Tara A., et al, *Neurosurgery*, (1994), vol. 34, No. 1, pp. 112–127.

Wilson, James T., et al, *The Journal of Trauma: Injury, Infection and Critical Care*, (1995), vol. 39, No. 3, pp. 473–477.

Cheng, Leland P., et al., "Inhibition of Myointimal Hyperplasia and Macrophage Infiltration by Estradiol in Aorta Allografts", *Transplantation*, vol. 52, No. 6, pp. 967–972 (1991).

Jacobsson, Jeanette, et al., "Effect of Estradiol on Accelerated Atherosclerosis in Rabbit Heterotopic Arotic Allografts", *Journal of Heart and Lung Translatation*, vol. 11, No. 6, pp. 1188–1193 (1992).

* cited by examiner

PRESERVATION OF TISSUE DURING REMOVAL STORAGE AND IMPLANTATION

CROSS REFERENCE

This application claims the benefit of the earlier Filing date of U.S. provisional patent application Ser. No. 60/009,705, filed Jan. 11, 1996, here incorporated by reference. The application is also a divisional application of U.S. Ser. No. 08/782,883 filed Jan. 10, 1997 now U.S. Pat. No. 5,824,672 which is a continuation-in-part of U.S. application Ser. No. 08/685,574, filed Jul. 24, 1996, now U.S. Pat. No. 5,859,001, all the above incorporated herein by reference.

This patent was created with support from the National Institute on Aging under grant number AG- 10485. The U.S. Government has certain rights to the invention.

TECHNICAL FIELD

The present invention relates to novel compositions and methods for the protection of tissues, cells, and organs during their removal from a donor, their storage, and their implantation into the recipient.

BACKGROUND

Preservation of the viability of cells in an organ or tissue during transplantation is problematic. The probability that a tissue will survive the process of transplantation depends on many factors including the status of the tissue prior to removal, the duration of time that the tissue remains outside the body and the procedure utilized to initiate reperfusion of the tissue in the recipient.

One source of injury that affects the success of tissue and organ transplantation is oxygen deprivation. In jury of organs, tissues, and cells occurs when the regular flow of oxygenated blood to the tissue and cells is interrupted. This occurs during surgical procedures to remove the organ from a living or recently deceased donor and subsequently during storage ex vivo prior to transplantation into a recipient. However, the most problematic stage in the transplantation process is the grafting of tissue into the recipient and reperfusion of the grafted tissue with oxygenated blood. When reperfusion occurs and energy metabolism starts up again, free radicals accumulate in the cells where anti-oxidant capacity has been diminished. The accumulation of free radicals contributes to post-transplantation injury in tissue giving rise to an increased number of damaged cells and an enhanced immune response by the recipient host. The immune response to transplanted cells includes inflammation caused by cellular antigens exposed by the damaged implanted cells.

Current attempts to reduce damage to tissues during transplantation rely on two general approaches. These are: 1) cooling the tissue to slow metabolic rate; and 2) minimizing the time between removal of the organ or the tissue from the donor and implantation of the tissue or organ into the recipient. During the time in which the body part is readied for transplantation, it is maintained in an isotonic solution. In addition, various investigators have explored the effect of adding anti-oxidants to cells and tissues in isotonic solution prior to implantation into a recipient. These antioxidants include alpha tocopherol (vitamin E), normally found in plasma membranes and membranes of the mitochondria and found to positively impact graft survival (Demirbas et al., Transplantation Proceetlings (1993) 25:2274; Ikeda et al. (1996) Life Sciences 59:781-8; Laue et al. (1995) Tranvsplantation Proceediings: 1875-6;); a compound (EPC-K1), a phosphodiester linkage between vitamin E and vitamin C (Tanemoto et al., Acta-Med-Okayama (1993) 47:121-7); 2-mercapto-imidazole derivatives (Chaudiere et al., WO 9,5 1 8,108); alpha keto-glutarate containing infusible compounds (Ekroth et al., WO 9,534,301); amino acids (Kramer et al., WO 9519768); creatine analogs (Elgebaly et al., WO 9,426,261); and ginkgolide (Ramwell et al., U.S. Pat. No. 5,002,965). In addition, monitoring of isotonic conditions has been found useful in reducing adverse effects on transplanted tissues. (Martindale et al., U.S. Pat. No. 5051352). In studies on the fate of transplant tissue after insertion into the recipient, Foegh et al. (1995) (Journal of Heart and Lung Transplantation (1995) vol. 14, p. S170) reported that estrogen attenuated transplant atherosclerosis by inhibiting abnormal cell growth of smooth muscle under transplant conditions.

There is a need for methods to improve the viability of cells removed from a donor, maintained outside of the body, and implanted into a recipient, such that cell damage is minimized thereby increasing the likelihood of a successful graft through improved viability of the cells and reduced problems resulting from adverse immune reactions.

SUMMARY

The present invention is directed to a method for enhancing cell viability in a population of graft cells during a transplantation procedure that includes the steps of selecting an effective dose of a polycyclic phenolic compound in a physiological acceptable formulation, exposing the population of araft cells to the formulation containing the compound within a time that is effectively proximate to the transplantation procedure, and conferring cytoprotection on the population of graft cells. The polycyclic compound may include a four ring, a three ring, or a two ring structure, having a molecular weight of less than 1000 Daltons. The compound may have a molecular weight of greater than 170 Daltons. The effective dose of the compound may achieve concentrations less than 200 nM or greater than 0.2 nM. The method may further comprise the step of exposing the graft cells to the compound prior to removal from the donor, during storage in vitro or during reperfusion in the recipient animal.

In a preferred embodiment of the invention, a method is provided for optimizing incorporation of graft cells into a recipient subject that includes the steps of selecting an effective dose of a polycyclic phenolic compound in a physiological acceptable formulation; and administering the compound to at least one of; the donor of the graft cells at an effective time prior to removal of the graft cells; the ex vivo storage medium for the graft cells; and the recipient subject at an effective time prior to receipt of the cells.

BRIEF DESCRIPTION OF THE DRAWINGS

These and other features, aspects and advantages of the present invention will become better understood with reference to the following description, appended claims and accompanying drawings where:

(A) treatment with a sham (empty) silastic pellet (sham), one week prior to implantation;

(B) treatment with a pellet containing 17β-estradiol (E2 group), one week prior to implantation.

Figure 3:
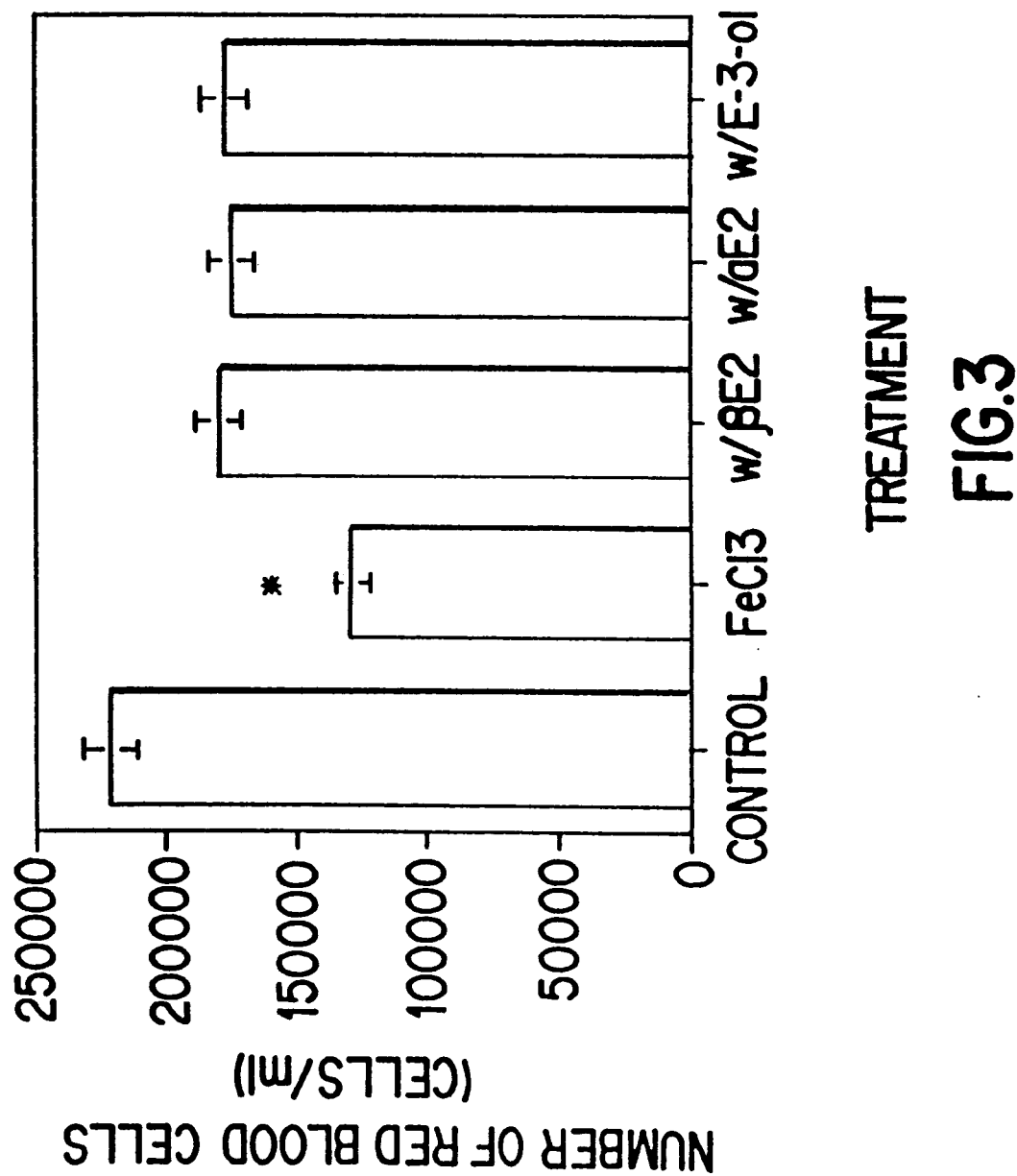

FIG. 3 shows the response of red blood cells to the addition of an oxidizing agent ($FeCl_3$) and the cytoprotective effect of three polycyclic phenols-17β-estrogen (βE2), 17α-estrogen (αE2) and estratriene-3-of (E-3-of) on cells treated with $FeCl_3$.

DETAILED DESCRIPTION

The need for a method to improve viability of cells during transplantation has been met by the inventive use of polycyclic phenolic compounds including estrogen compounds that have been found to act effectively to protect cells from damage and death in conditions where an oxygen deficit or other type of damage has occurred.

An animal subject is defined here and in the claims as inclusive of human subjects.

Estrogen compounds are defined here and in the claims as any of the structures described in the 11 th edition of "Steroids" from Steraloid Inc., Wilton, N. H., here incorporated by reference. Included in this definition are non-steroidal estrogens described in the aforementioned reference. Other estrogens included in this definition are estrogen derivatives, isomers, estrogen metabolites, estrogen precursors, and modifications of the foregoing as well as molecules capable of binding cell associated estrogen receptor as well as other molecules where the result of binding triggers a characteristic estrogen effect. Also included are mixtures of more then one estrogen.

Graft cells protected by the invention include those cells, tissues or organs obtained from a donor for transplantation into a recipient where the graft cells may be derived from human subjects or from animals and may be transplanted from one subject back into the same subject or from one subject (the donor) into another subject (the recipient) for the purpose of improving the health of the recipient. The donor subject can be a living subject, fetus, or a recently dead subject. The grafts include replenishable cells taken from a healthy donor such as stem cells, blood cells, bone marrow cells, placental cells, liver cells, sperm, and ova. Also included are organs removed from a healthy donor such as the kidney as well as organs removed from a cadaver at point of death including heart, lungs, and corneal tissue. This last group includes fetal tissue such as brain tissue taken from an aborted fetus.

Tissues that are protected by the method of the invention may be derived from children, adult or fetal tissue and include, but are not limited to, blood and all of its components, including erythrocytes, leukocytes, platelets, serum, central nervous tissue, including brain and spinal cord tissue, neurons, and glia; peripheral nervous tissue, including ganglia, posterior pituitary gland, adrenal medulla, and pineal; connective tissue, including skin, ligaments, tendons, and fibroblasts; muscle tissue, including skeletal, smooth and cardiac tissues or the cells therefrom; endocrine tissue, including anterior pituitary gland, thyroid gland, parathyroid gland, adrenal cortex, pancreas and its subparts, testes, ovaries, placenta, and the endocrine cells that are a part of each of these tissues; blood vessels, including arteries, veins, capillaries and the cells from these vessels, lung tissue; heart tissue and whole organ; heart valves; liver; kidney; intestines; bone; immune tissue, including blood cells, bone marrow and spleen; eyes and their parts; reproductive tract tissues; and urinary tract tissue.

The methods of the invention may be applied to the process of blood transfusions in which erythrocytes are transferred from an animal donor back to the donor or to an animal recipient or archived indefinitely. Additional applications include storage and protection of a tissue or tissue type during transplantation, for example, fetal tissue for fetal brain transplants in the treatment of Parkinson's disease, the heart during transplantation, and body parts for reattachment after accidental severance.

The donor and/or recipient of the tissue protected by this invention is not species restricted but may be applied to tissue from any animal, including mammals, such as domestic animals, for example, pigs, cows and sheep, and primates as well as humans. This invention is directed to transplantation of tissue from one member to another of the same species or back to the same individual as well as from a member of one species to a member of another species.

The methods of the invention may be applied to any or all of the procedures involving perfusing the tissue at a time that is effectively proximate to excision from the donor, perfusing or immersing or otherwise exposing the tissue to the described compounds during storage, and perfusing or otherwise treating the tissue after its transplantation into the recipient. An effective proximate time may include the administration of polycyclic compound to achieve an effective dose within the target tissue beginning approximately 1 week prior to the procedure of removal or introduction of tissue. The compound may be utilized in the medium of cells, tissues or organs ex vivo for up to the entire incubation or storage period of the graft cells.

The use of cytoprotective compounds of the invention result in an improved outcome for cell, organ, and tissue transplantation by reducing the damage to the tissue that leads to decreased viability of the cells during transplantation.

The cytoprotective compounds of the invention include, but are not limited to, the class of phenolic A ring compounds containing the cyclopentanophen[a]anthrene ring structure that are steroidal in structure as well as related classes of compounds that contain a phenolic ring but are non-steroidal in structure. In a particular embodiment of the invention, the size of the compounds of invention is less than 1000 Daltons and in certain embodiments may be larger than 170 Daltons. In a further embodiment, the size range of the compounds are between 170–100) Daltons. The polycyclic phenolic compound may be formulated in a physiologically acceptable formulation in a manner that is consistent with the art.

The preferred embodiment of the invention includes a compound having a terminal phenolic ring and at least a second carbon ring. In addition to these required structures, the compound may have a number of R groups attached to any available site on the phenolic ring or elsewhere providing that the phenolic structure of the terminal ring is maintained. These R-groups may be selected from inorganic or organic atoms or molecules. Examples of compounds having utility in the invention are provided in parent application, Ser. No. 08/685,574, now U.S. Pat. No. 5,859,001, incorporated here by reference. Compounds for use in the invention include estrogen compounds.

In a particular embodiment of the invention, the dose of the compound may provide a tissue concentration of less than 200 nM, or may provide a tissue concentration of greater than 0.2 nM.

According to the invention, it has been shown that a polycyclic phenolic compound when administered to the donor animal prior to surgery enhances the viability of the cells after their removal. Example 1 demonstrates the beneficial effect of pretreating a rat model with 17β-estradiol prior to removal of muscle tissue. Once isolated, polycyclic phenolic compounds have been shown to protect erythrocytes (red blood cells) from death induced by $FeCl_3$ induced oxidative distress. (Example 2) The beneficial effect of pretreating the recipient animal with a polycyclic phenolic compound prior to implantation of tissue has been demonstrated in Example 3, where pretreatment of the animal recipient (rat) with 17β-estradiol enhances the viability of the transplanted neuronal cells during reperfusion. The neuroprotective effects of maintaining cells (SK—N—SH neurons) in the presence of an estrogen compound in vitro has been demonstrated in Example 1 and Example 2 of Ser. No. 08/685,574, now U.S. Pat. No. 5,859,001, incorporated herein by reference.

EXAMPLES

Example 1

Increased viability of graft cells when the animal donor is treated with a polycyclic phenolic compound prior to removal of graft cells from the donor.

This example demonstrates the beneficial effect of pretreating a subject with a polycyclic phenolic compound prior to removal of tissue, organs or cells for storage or transplantation. In particular, rats were here treated with an estrogen compound prior to removal of muscle tissue from the donor animal. The status of the isolated muscle tissue was followed by measuring levels of creatine kinase, a muscle specific enzyme, in the isotonic medium in which the muscle was subsequently maintained.

One week prior to removal of muscle, rats were treated with 17β-estradiol (E2) packed in 5 mm silastic tubes inserted subcutaneously, according to the method of Mohammed et al. (1985) Ann. Neurol. 18, 705–71 1. Muscle tissue was removed and damage to the tissue was assessed by the in vitro basal cumulative release of creatine kinase over four hours. The extensor digitorum longus (EDL) and the soleus (SOL) muscle were isolated from ovariectomized animals (OVX), Sham (SHAM) controls and Ovariectomized animals supplemented with estradiol (OVX+E2) for two weeks. The OVX+E2 animals were supplemented with estrogen for two weeks to achieve plasma E2 levels of approximately twice those in the SHAM animals. Serum estradiol levels at the end of the two week period were 32.3, 20.0 and 56.5 pg/ml of the SHAM, OVX and OVX+E2 animals, respectively. The animals were humanely sacrificed and the SOL and EDL muscles harvested via the tendons and placed into a carboxygenated balanced salt solution (pH7.4) at 37°.

Figure 1:
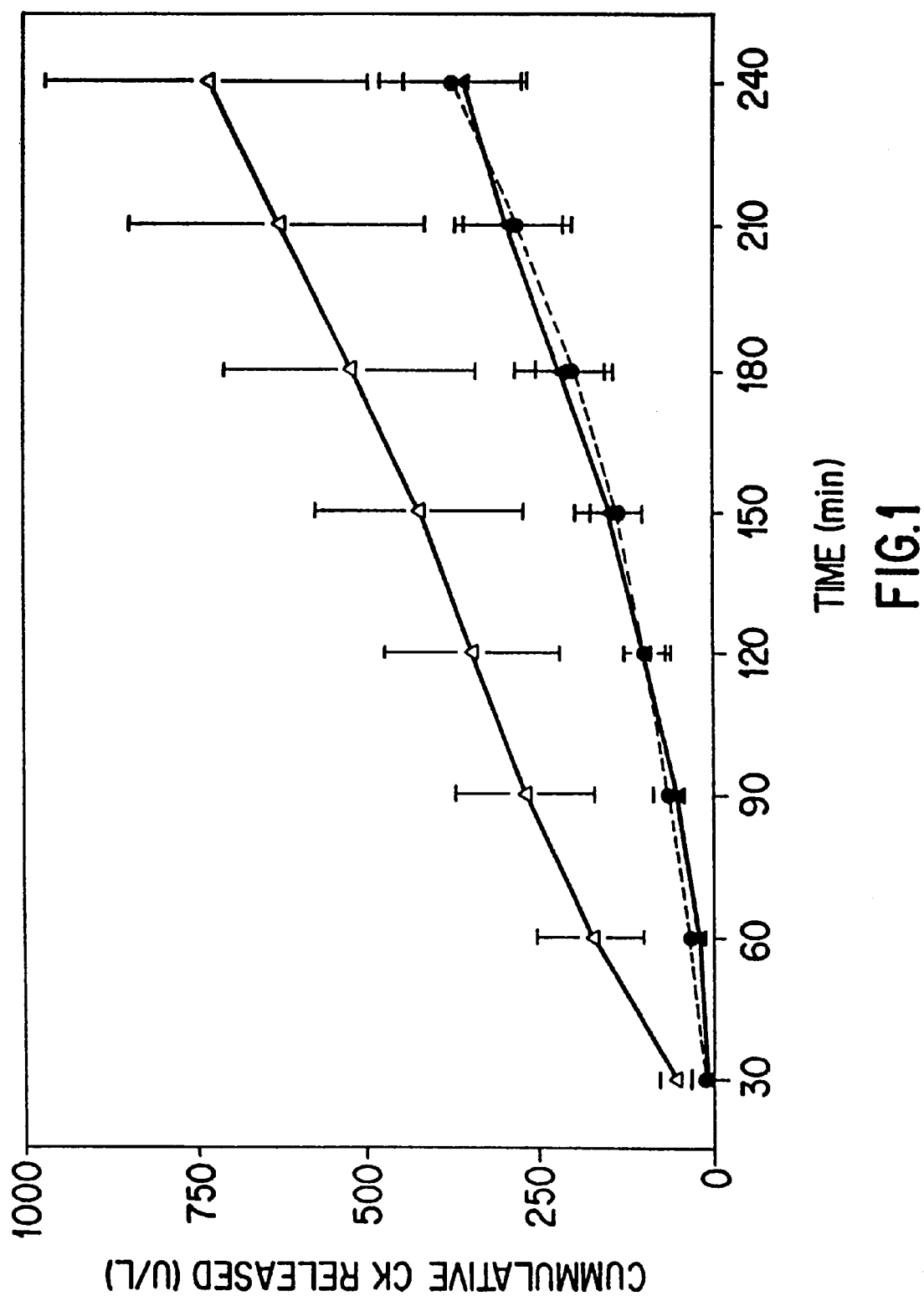
FIG. 1 shows in vitro cumulative creatine kinase release from the soleus muscles, a function of time after removal from rats. Open triangles indicate ovariectomized donor animals, closed circles indicate ovary intact donor animals, closed triangles indicate ovariectomized plus 17-β estradiol-replaced donor animals. Depicted are the mean+SEM. Muscle from ovariectomized donor rats released significantly more creatine kinase than those from either ovary-intact or estrogen-replaced donor animals.
Figure 2A:
FIG. 2 shows a photomicrograph (4×magnification) of a brain section containing SK—N—SH cell implanted into the corpus callosum of an ovariectomized rat. Samples were obtained at one week following transplantation.
Figure 2B:

As shown in FIG. 1, there was no significant treatment differences in the plasma creatine kinase levels and total basal cumulative creatine kinase release from the EDL muscle among the three groups. In contrast, the basal cumulative release of creatine kinase from the SOL muscle of the OVX animals was statistically higher compared to SHAM animals (FIG. 1). The cumulative creatine kinase release from ovariectomized animals which were supplemented with E2 (OVX+E2) was significantly lower than OVX animals and equivalent to that of the SHAM controls. At the end of the four-hour period, to eliminate any potential discrepancies in cytosolic enzyme release as a function of total muscle creatine kinase, the muscles were homogenized and total remaining enzyme activity measured. There was no statistical difference among the treatment groups with respect to total muscle creatine kinase thereby demonstrating the protective effect of estrogen on skeletal muscle.

Example 2

Increased viability of graft cells in the recipient when the recipient is treated with polycyclic compounds prior to reperfusion of the graft cells.

This example demonstrates the beneficial effect of pretreating a subject with a polycyclic phenolic compound prior to implantation of tissue, organs or cells from an external source. In particular, rats were here treated with an estrogen compound prior to introduction of neuronal (SK—N—SH) cells. The status of the implanted neuronal cells was established by observing histological sections of the brain after sacrifice of the animal.

The ability of a polycyclic phenolic compound to protect tissue during reperfusion in the recipient was determined as follows.

Adult female Charles River CD rats were ovariectomized and implanted with a sham (empty) silastic pellet (sham group) or with a pellet containing 17β-estradiol (E2 group). One week later both sham and E2 groups were subjected to a neurosurgical implantation of SK—N—SH human neuronal cells into the corpus callosum. Prior to implantation, the SK—N—SH cells had been grown in vitro in the absence of steroid hormones. The animals were sacrificed at 1 week after implantation and the brains were surgically removed, cut into 4PM sections and stained with cresyl violet.

In sham animals, SK—N—SH cells were observed to be clumped at the injection site, and at various other locations. By contrast, in E2 pretreated animals the SK—N—SH were well distributed without clumping of cells. The clumping of cells represents a lack of success of the transplantation in as much as these clumped cells are not interacting with the host tissue. By contrast, SK—N—SH cells transplanted into E2-treated rats appeared to grow out from the injection site.

The beneficial effect of treating the recipient with a polycyclic phenolic compound exemplified by 17β-estradiol, prior to receipt of transplanted tissue was thus established. The experimental method disclosed in this example may be used in a routine manner to test any selected polyphenolic compound.

Example 3

Increased viability of graft cells ex vivo when media is treated ex vivo with polycyclic phenolic compounds.

The ability of polycyclic phenolic compounds to protect graft cells in vitro following their removal from a human subject was demonstrated using isolated erythrocytes. These cells were exposed to $FeCl_3$ which serves as an oxidizing agent to mimic conditions commonly encountered by tissues and organs when removed from the host. This insult is particularly relevant to tissues with a high iron content Such as erythrocytes and spleen cells. A blood sample was withdrawn from an adult male human subject and centrifuged to collect erythrocytes. The erythrocytes were then washed with isotonic physiological saline. Cells were then incubated with 200μM $FeCl_3$ or with 200μM $FeCl_3$ in the presence of 20 nM 17 β-estradiol, 17β-estradiol or estratriene-3-ol for 4 hours at 37° C. At the end of 4 hours incubation period the remaining cells were counted. Cells that were untreated with $FeCl_3$ served as controls. As shown in FIG. 3, treatment with $FeCl_3$ reduced erythrocyte numbers by 42% versus untreated controls (p,0.05). By contrast, erythrocytes treated with 17β-estradiol, 17β-estradiol or estratriene-3-ol failed to exhibit a significant reduction in cell numbers in response to $FeCl_3$ treatment.

These results demonstrate that in vitro treatment of erythrocytes with polycyclic compounds provides protection from oxidative stress-induced cell death.

We claim:

1. A method for enhancing cell viability in a population of graft cells during a transplantation procedure, comprising:
   (a) selecting an effective dose of a polycyclic phenolic compound in a physiologically acceptable formulation;
   (b) exposing the population of graft cells to the formulation containing the compound within a time that is effectively proximate to the transplantation procedure: and
   (c) conferring cytoprotection on the population of graft cells.

2. The method according to claim 1, wherein the polycyclic phenolic compound has a molecular weight of less than 1000 Daltons.

3. The method according to claim 1, wherein the polycyclic phenolic compound has a molecular weight of greater than 170 Daltons.

4. A method according to claim 2, wherein the compound comprises a three-ring structure.

5. A method according to claim 2, wherein the compound comprises a two ring compound.

6. A method according to claim 4, wherein the three-ring structure is a phenanthrene compound.

7. A method according to claim 1, wherein the effective dose provides a tissue concentration of the compound that is equal to or less than 200 nM.

8. A method according to claim 1, wherein the effective dose provides a tissue concentration of the compound that is equal to or greater than 0.2 nM.

9. A method according to claim 1, further comprising exposing the population ot graft cells to the compound prior to removal from a donor animal.

10. A method according to claim 1, further comprising exposing the population of graft cells to the compound during storage in an isotonic solution following removal from a donor animal.

11. A method according to claim 10, further comprising exposing the recipient to the compound prior to reperfusion of the population of graft cells.

12. A method of optimizing incorporation of graft cells into a recipient subject comprising;
   (a) selecting an effective dose of a polycyclic phenolic compound in a physiological acceptable formulation; and
   (b) administering the compound to at least one of; the donor of the graft cells at an effective time prior to removal of the graft cells; the ex vivo storage medium for the graft cells; and the recipient subject at an effective time prior to receipt of the cells.

13. The method according to claim 12, wherein the polycyclic phenolic compound has a molecular weight of less than 1000 Daltons.

14. The method according to claim 12, wherein the polycyclic phenolic compound has a Molecular weight of greater than 170 Daltons.

15. A method according to claim 13, wherein the compound comprises a three-ring structure.

16. A method according to claim 13, wherein the compound comprises a two ring compound.

17. A method according to claim 15, wherein the three-ring structure is a phenanthrene compound.

18. A method according to claim 12, wherein the effective dose provides a tissue concentration of the compound that is equal to or less than 200 nM.

19. A method according to claim 12, wherein the effective dose provides a tissue concentration of the compound that is equal to or greater than 0.2 nM.

* * * * *